United States Patent [19]

Takaoka et al.

[11] Patent Number: 5,637,474
[45] Date of Patent: Jun. 10, 1997

[54] PROCESS FOR MEASURING AMOUNT OF ENDOTOXIN OR (1→3)-β-D-GLUCAN BY KINETIC TURBIDIMETRIC METHOD

[75] Inventors: Aya Takaoka; Masakazu Tsuchiya; Keiko Kawabe; Haruhisa Ijiri, all of Amagasaki, Japan

[73] Assignee: Wako Pure Chemical Industries, Ltd., Osaka, Japan

[21] Appl. No.: 545,290

[22] Filed: Oct. 19, 1995

[30] Foreign Application Priority Data

Oct. 31, 1994 [JP] Japan ................................. 6-290596

[51] Int. Cl.⁶ .............................. C12Q 1/34; C12Q 1/04
[52] U.S. Cl. .............................. 435/18; 435/23; 435/34
[58] Field of Search ............................ 435/4, 18, 23, 435/34

[56] References Cited

U.S. PATENT DOCUMENTS

| | | | |
|---|---|---|---|
| 4,221,865 | 9/1980 | Dubczak et al. | 435/4 |
| 4,221,866 | 9/1980 | Cotter | 435/4 |
| 4,273,557 | 6/1981 | Juranas | 23/230 B |
| 5,318,893 | 6/1994 | Matuura et al. | 435/23 |

FOREIGN PATENT DOCUMENTS

| | | |
|---|---|---|
| 0173021A3 | 3/1986 | European Pat. Off. |
| 0569033A2 | 11/1993 | European Pat. Off. |
| 2080524 | 2/1982 | United Kingdom . |

OTHER PUBLICATIONS

Database WPI, week 9539; Derwent Publications Ltd., London GB; AN 95-295935 & JP-A-07 191 038 (Wako Pure Chem Ind. Ltd.) 28 Jul. '95 (Abstract).

*Primary Examiner*—Ralph Gitomer
*Attorney, Agent, or Firm*—Armstrong, Westerman, Hattori, McLeland & Naughton

[57] ABSTRACT

A process for measuring the amount of endotoxin or (1→3)-β-D-glucan (referred to hereinafter as β-glucan) contained in a sample, which comprises mixing the sample with amebocyte lysate of horseshoe crabs in the presence of at least one water-soluble polymer selected from the group consisting of a polyethylene glycol, a polyvinyl alcohol, a methyl cellulose and a hydroxypropyl cellulose, applying a light to the resulting mixture, measuring the time required until a degree of optical variation of the resulting mixture reaches a predetermined value after the mixing of the sample with the amebocyte lysate, or after the lapse of the predetermined time from the mixing of the sample with the amebocyte lysate, and determining the amount of endotoxin or β-glucan contained in the sample on the basis of the relationship between the said time and the amount of endotoxin or β-glucan; and also a reagent for measuring the amount of endotoxin or β-glucan contained in a sample, which comprises amebocyte lysate of horseshoe crabs and at least one water-soluble polymer selected from the group consisting of a polyethylene glycol, a polyvinyl alcohol, a methyl cellulose and a hydroxypropyl cellulose.

4 Claims, No Drawings

PROCESS FOR MEASURING AMOUNT OF ENDOTOXIN OR (1→3)-β-D-GLUCAN BY KINETIC TURBIDIMETRIC METHOD

BACKGROUND OF THE INVENTION

This invention relates to a process for measuring the amount of endotoxin or (1→3)-β-D-glucan (referred to hereinafter as β-glucan) contained in a sample which comprises reacting the endotoxin or β-glucan with amebocyte lysate of horseshoe crabs and analyzing the reaction mixture by a kinetic turbidimetric method.

Endotoxin is a substance present in cell walls of Gram-negative bacteria and has various biological activities such as fervescence and the like. Therefore, when medical devices which contact directly with drugs or blood are contaminated with endotoxin, a grave result is brought about in some cases even if the amount of the endotoxin is very slight. Hence, the contamination with endotoxin must be controlled strictly. Also, for early diagnosis of septicemia due to Gram-negative bacteria, the quantitation of the endotoxin in blood has been tried.

Also, the β-glucan is a substance which is known to exist as a skeleton constituent of cell walls of yeasts and molds, as an important polysaccharide component of many basidiomycetes fruit bodies (mushroom), as an eluate component from a membrane or the like used in the hemodialysis, or the like. The biological activity of the β-glucan is not so clear as in the case of the endotoxin; however, it has been considered that early diagnosis of mycosis and detection of contamination of medical devices with fungi be made possible by measuring the amount of the β-glucan.

Each of the endotoxin and β-glucan is known to react with a solution containing amebocyte lysate of horseshoe crabs (referred to hereinafter as the AL solution) to activate an enzyme and cause gelation reaction. Utilizing such properties, various methods for measuring the amount of the endotoxin or β-glucan contained in a sample have been developed and utilized.

Representative examples of the measurement method utilizing the gelation reaction which is caused between the AL solution and the endotoxin (or the β-glucan) include a so-called gel-clot method in which it is visually confirmed whether or not gelation is caused and so-called kinetic turbidimetric method such as a method for determining the amount of the endotoxin (or β-glucan) contained in a sample on the basis of the relationship between the endotoxin (or β-glucan) concentration and the gelation time determined by measuring the time required until a varied degree of the transmitted light amount ratio ($R_t$) [the ratio between the transmitted light amount at the initial stage ($I_0$) and the transmitted light amount ($I_t$) after the time t elapsed from the mixing of the sample with the AL solution or from the lapse of predetermined time from the mixing of the sample with the AL solution, $R_t=I_t/I_0$] which ratio is reduced by gelation reaction or a varied degree of a logarithmic value of the ratio $R_t$ reaches a predetermined value, a method for determining the amount of the endotoxin (or β-glucan) in a sample from the relationship between the endotoxin (β-glucan) concentration and the onset time determined by measuring the time required until a varied degree of the change of transmittance or absorbance due to gelation reaction reaches a predetermined value, etc.

Among these methods, the kinetic turbidimetric method is simpler and has a higher sensitivity than the gel-clot method and hence has been widely used.

However, the detection limit of endotoxin by the current kinetic turbidimetric method is usually about 0.001EU/ml, and hence, a measuring method having such a high sensitivity that much less endotoxin can be detected has been desired.

On the other hand, U.S. Pat. No. 4,221,865 disclose a process for determining endotoxin improved in the measurement sensitivity and enhance the reproducibility in a nephelometric method by allowing both ionic surfactant and suspending agent or a polymer having simultaneously the properties of the two to be present during the reaction between the AL solution and the endotoxin (or β-glucan). According to this U.S. Patent, an ionic surfactant is added so as to stop the coagulation of Limulus protein, and a suspending agent is added to stabilize pharmaceutical or food emulsions and colloidal solutions.

However, this method must use two reagents of surfactant and suspending agent, so that there are such problems that the operation becomes complicated and the possibility that the AL solution is contaminated with the endotoxin or β-glucan present in the reagents is high. Therefore, a further improvement is desired even at present.

SUMMARY OF THE INVENTION

It is an object of this invention to provide a process for measuring the amount of the endotoxin and β-glucan contained in a sample by the kinetic turbidimetric method which process has such a high sensitivity that much less endotoxin or β-glucan can be detected than by conventional methods.

Other objects and advantages of this invention will become apparent from the following description.

According to this invention, there is provided a process for measuring the amount of the endotoxin or β-glucan contained in a sample which comprises:

mixing a sample containing endotoxin or β-glucan with amebocyte lysate of horseshoe crabs in the presence of at least one water-soluble polymer selected from the group consisting of polyethylene glycol, polyvinyl alcohol, methyl cellulose and hydroxypropyl cellulose, applying a light to the resulting liquid mixture, measuring the time required until a degree of optical variation of the liquid mixture reaches a predetermined value after the mixing of the sample with the amebocyte lysate, or after the lapse of the predetermined time from the mixing of the sample with the amebocyte lysate, and determining the amount of the endotoxin or β-glucan contained in the sample on the basis of the correlation between the said time and the amount of endotoxin or β-glucan.

The present invention also provides a reagent for measuring the amount of endotoxin or β-glucan contained in a sample, which comprises amebocyte lysate of horseshoe crabs and at least one water-soluble polymer selected from the group consisting of a polyethylene glycol, a polyvinyl alcohol, a methyl cellulose and a hydroxypropyl cellulose.

DESCRIPTION OF THE PREFERRED EMBODIMENTS

In the so-called kinetic turbidimetric method such as a method for determining the amount of the endotoxin (or β-glucan) contained in a sample on the basis of the relationship between the endotoxin (or β-glucan) concentration and the gelation time determined by measuring the time required until a varied degree of the transmitted light amount ratio $R_t$ [the ratio between the transmitted light amount ($I_0$) at the initial stage and the transmitted light amount ($I_t$) after the lapse of the predetermined time (t), $R_t=I_t/I_0$] or a varied degree of a logarithmic value of the ratio $R_t$, which ratio is reduced by gelation reaction caused as a result of the reaction between the AL solution and the endotoxin (or β-glucan), reaches a predetermined value; a method for determining the amount of the endotoxin (or β-glucan) contained in a sample from the relation between the endotoxin (β-glucan) concentration and the onset time determined by measuring the time required until the change of transmittance or absorbance due to the gelation reaction reaches a predetermined value; etc., the gelation reaction can be effectively accelerated by making a specific water-soluble polymer present without co-using an ionic surfactant in the reaction system during the reaction of the AL solution with the endotoxin (or β-glucan). In other words, that both the shortening of the reaction time in the kinetic turbidimetric method and the enhancement of the measurement sensitivity of the kinetic turbidimetric method are achieved by using only the specific water-soluble polymer without using an ionic surfactant.

As mentioned above, the ionic surfactant is not used fundamentally in the present invention. Since the ionic surfactant has, for example, a function of stopping the reaction between the amebocyte lysate of horseshoe crabs and endotoxin (or β-glucan), a function of precipitating a component in the AL solution (not a gel caused by the reaction with endotoxin or β-glucan), etc., when the ionic surfactant is used in a conventionally used amount (e.g. the concentration of 0.5 to 20% by weight in a solution as taught by U.S. Pat. No. 4,221,865), the improvement in the sensitivity in the kinetic turbidimetric method according to the present invention (in other words, the improvement of measuring sensitivity due to shortening of the reaction time) cannot be attained.

Among the specific water-soluble polymers used in this invention, the polyethylene glycol preferably has a weight-average molecular weight of 3,000 to 4,000,000, more preferably 7,500 to 70,000. When the weight-average molecular weight is too small, the gelation accelerating action is weak and when it is too larger, the viscosity of a solution containing the polyethylene glycol becomes high and the handling thereof becomes difficult. For the same reason as above, the polyvinyl alcohol has preferably a degree of polymerization of 500 to 2,000.

The concentration of the specific water-soluble polymer used in the gelation reaction caused as a result of the reaction of endotoxin (or β-glucan) with the AL solution (referred to hereinafter as the concentration used in gelation reaction) may be somewhat varied depending upon the kind, molecular weight, degree of polymerization and the like of the water-soluble polymer used and on the kind and lot of the AL solution used; however, it is appropriately selected from the range of 0.5 to 4 w/w % when, for example, a polyethylene glycol having a weight-average molecular weight of about 3,000 is used; from the range of 0.3 to 4 w/w % when a polyethylene glycol having a weight-average molecular weight of about 7,500 is used; from the range of 0.3 to 1.5 w/w % when a polyethylene glycol having a weight-average molecular weight of 20,000 to 70,000 is used; or from the range of 0.2 to 0.5 w/w % when a polyethylene glycol having a weight-average molecular weight of 500,000 to 4,000,000 is used. Also, the concentration used in gelation reaction is appropriately selected from the range of 1 to 3 w/w % when a polyvinyl alcohol having a degree of polymerization of about 500 is used; from the range of 0.2 to 1 w/w % when a polyvinyl alcohol having a degree of polymerization of about 2,000 is used; from the range of 0.2 to 1 w/w/ % when a methyl cellulose having a viscosity of about 15 cps is used; from the range of 0.1 to 1 w/w % when a methyl cellulose having a viscosity of about 100 cps is used; or from the range of 0.1 to 1 w/w % when a hydroxypropyl cellulose is used.

These water-soluble polymers have a sufficient effect even when each thereof is used alone; however, they may be used in appropriate combination of two or more.

The water-soluble polymers used in this invention must not, as a matter of course, contain endotoxin or β-glucan in such an amount as to affect the measurement of the amount of the endotoxin or β-glucan contained in a sample. For this purpose, a water-soluble polymer having a small endotoxin or β-glucan content is selected, or alternatively, when the water-soluble polymer used contains endotoxin and β-glucan in a significant amount, the water-soluble polymer is required to be previously freed from the endotoxin and β-glucan using an autoclave, an endotoxin-absorber or the like.

When the removal of the endotoxin and β-glucan is carried out using an autoclave, it is sufficient, for example, to form the above-mentioned water-soluble polymer into a solution having a suitable polymer concentration and then subject the same to an autoclave treatment at, for example, a usual temperature (about 121°) for about 15 to 120 minutes.

When the removal of the endotoxin using an endotoxin-absorber, there may be used, for example, a carrier on which polymyxin B has been fixed, a carrier on which histidine has been fixed through a spacer, or the like. Specifically, Detoxi-Gel (a trade name of PIERCE), Affi-Prep Polymyxin (a trade name of Bio-Rad Laboratories), Pyro Sep (a trade name of TANABE SEIYAKU CO., LTD.) and the like may be used; however, the endotoxin-absorber is, of course, not limited to these examples.

In the process of this invention, there can be used the optical variation which is used as an index for measuring the endotoxin (or β-glucan) concentration in a sample and resulting from the gelation reaction caused as a result of reaction between the AL solution and the endotoxin (or β-glucan). For example, an optical variation caused by the change in transmittance, the change in absorbance, the varied degree of the transmitted light amount ratio $R_t$, the varied degree of logarithmic value of the transmitted light amount ratio $R_t$, or the like used as a measurement index in the so-called kinetic turbidimetric method are preferred.

The ambocyte lysate of horseshoe crabs used in this invention is not critical; and may be lysate from amebocyte of horseshoe crabs belonging to, for example, the Limulus genus, the Tachypleus genus, etc., which lysate increases the turbidity upon reacting with the endotoxin or β-glucan. As a matter of course, there can be used, for example, those prepared from freeze-dried products of the AL solutions commercially available from ACC (Associates of Cape Cod), Whittaker Bioproducts, Inc., Endosafe, Inc., Seikagaku Corp., Wako Pure Chemical Industries, Ltd. and the like.

In carrying out the process of this invention, the above-mentioned water-soluble polymer is added to and dissolved in the reaction mixture of the AL solution with the endotoxin (or β-glucan) so that the concentration used in gelation reaction becomes a predetermined concentration, and the solution thus obtained is subjected to measurement of the amount of endotoxin (or β-glucan) by a kinetic turbidimetric method in a conventional manner.

The method of measuring the amount of the endotoxin (or β-glucan) contained in a sample by a kinetic turbidimetric method unitizing the process of this invention is explained below.

Preferable procedures of the method are, for example, in accordance with the kinetic turbidimetric method stated in FDA guideline [Guideline on validation of the Limulus amebocyte lysate test as an end-product endotoxin test for human and animal parenteral drugs, biological products, medical devices, Food and Drug Adm. (1987)].

More specifically, it is sufficient to carry out the measurement by the kinetic turbidimetric method using the AL solution utilizing an exclusive apparatus such as Toxinometer ET-201 (a trade name of Wako Pure Chemical Industries, Ltd.), Toxinometer ET-251 (a trade name of Wako Pure Chemical Industries, Ltd.), Toxinometer ET-301 (a trade name of Wako Pure Chemical Industries, Ltd.), LAL-5000 [a trade name of ACC (Associates of Cape Code) company], Microplate reader $T_{max}$ (a trade name of Molecular Device Company) and the like.

That is to say, for example, the following operation may be conducted using the above apparatus:

First of all, amebocyte lysate of horseshoe crabs is mixed with a sample containing endotoxin or β-glucan in the presence of at least one water-soluble polymer selected from the group consisting of a polyethylene glycol, a polyvinyl alcohol, a methyl cellulose and a hydroxypropyl cellulose, a light is applied to the resulting liquid mixture, and subsequently, the liquid mixture is subjected to measurement of the time required until a degree of optical variation such as a change in transmittance, a change in absorbance, a varied degree of transmitted light amount ratio $R_r$, a varied degree of logarithmic value of the transmitted light amount ratio $R_t$ or the like reaches a predetermined value after the mixing of the sample with the amebocyte lysate, or after the lapse of the predetermined time from the mixing of the sample with the amebocyte lysate. On the basis of the correlation between the time thus obtained and the amount of endotoxin or β-glucan (for example, utilizing the previously obtained calibration curve between said time and the amount of endotoxin or β-glucan), the amount of the endotoxin or β-glucan contained in a sample can be determined.

In the above explanation, the starting point of the time required until a degree of the optical variation reaches a predetermined value is a point of time at the mixing of the sample with the amebocyte lysate, or a point of time with the lapse of a predetermined time from the mixing of the sample with the amebocyte lysate. Although the predetermined time is not critical and varied depending on the activity (or measurement sensitivity) of the amebocyte lysate for endotoxin or β-glucan etc., it is generally in the range of 2 or 3 seconds to 3 to 5 hours, according to the object of the measurement.

The predetermined time can be determined considering the following points:

a) the time which does not interfere with the measurement of endotoxin or β-glucan, b) the time which is sufficiently short compared with the time required for actually starting the optical variation of the resulting mixture after the mixing of the sample with the amebocyte lysate, and c) the time which makes a measuring error within ±25% even if such a measuring error occurs, since an allowable error in the endotoxin measurement is within ±25% to the true value according to the FDA guideline for measurement of endotoxin by kinetic turbidimetric method.

For example, when the amount of endotoxin in a water for injection is measured so as to judge whether or not the amount of endotoxin is over the maximum permissible limit (i.e. about 0.25 EU/ml) by using an AL solution having such a measurement sensitivity that the measurement can be finished within 30 minutes on a sample containing over the permissible amount of endotoxin, the predetermined time is generally in the range of 2 or 3 seconds to 2 or 3 minutes.

When the measurement is conducted by utilizing an apparatus for the kinetic turbidimetric method, the staring point may be a point of time at the mixing of the sample with the amebocyte lysate, or a point of time at which a measuring test tube containing these mixture is set in the apparatus. In this case, when a number of measuring test tubes are set in the apparatus immediately after the mixing of the sample with the amebocyte lysate, the starting point for the measurement for each test tube may be different so far as the difference in the starting point is within a few seconds, because such a time difference usually may not cause a significant error in the measurement.

In order to obtain the time (e.g. gelation time, onset time, etc.) in the measurement of amount of endotoxin (or β-glucan) according to the present invention, a predetermined value for the degree of optical variation is set previously in the range which is sufficient to achieve an objective measurement. When the optical variation is caused by a varied degree of the transmitted light amount ratio $R_r$, for example, the predetermined value is appropriately in the range of −3 to −25%, preferably −5 to −20%. Also, when the optical variation is caused by a change of transmittance, a change of absorbance, a varied degree of the logarithmic value of the transmitted light amount ratio $R_r$, or the like, the predetermined value may be selected in accordance with the case of the transmitted light amount ratio $R_t$".

The method of adding the water-soluble polymer to be used in this invention to the reaction mixture of amebocyte lysate of horseshoe crabs with endotoxin (or β-glucan) so that the polymer concentration becomes a predetermined value may be a method by which the water-soluble polymer can be added to the reaction mixture of amebocyte lysate of horseshoe crabs with endotoxin (or β-glucan) so that the final concentration of the polymer becomes the predetermined concentration; however, this method is not critical, and there may be preferably used, for example, a method in which the AL solution containing the water-soluble polymer in the predetermined concentration is freeze-dried and then dissolved again and used; a method in which an appropriate amount of the water-soluble polymer is added to and dissolved in the AL solution; a method in which the freeze-dried product of the AL solution is dissolved in an aqueous solution containing the water-soluble polymer; a method in which a sample (containing endotoxin or β-glucan) to be measured is appropriately diluted with an aqueous solution containing the water-soluble polymer; and the like.

Incidentally, it is needless to say that the aqueous solution containing the water-soluble polymer may contain, for example, a buffering agent such as phosphoric acid buffer, Good's buffer or the like in such an amount that the measurement of the amount of endotoxin or β-glucan may not be inhibited nor accelerated.

The measuring reagent of this invention is used for carrying out the above process for measuring the amount of the endotoxin or β-glucan contained in a sample and contains amebocyte lysate of horseshoe crabs and a water-soluble polymer selected from the group consisting of a polyethylene glycol, a polyvinyl alcohol, a methyl cellulose and a hydroxypropyl cellulose. The preferable modes, embodiments and the like of the respective constructive elements are as mentioned above. Also, the measuring reagent of this invention may contain, in addition to the above-mentioned components, a buffer such as a phosphoric acid buffer, a Good's buffer or the like in such an amount that the measurement of the amount of endotoxin or β-glucan is not inhibited nor accelerated.

Examples are shown below to explain more specifically this invention; however, this invention should not be construed to be limited to the Examples.

EXAMPLE 1

(Reagents)

Endotoxin solution

*Escherichia coli* reference endotoxin (the standard endotoxin defined in Pharmacopoeia of Japan, lipopolysaccharide resulting from *E. coli* UKT-B strain, containing endotoxin in an amount corresponding to 16,000 endotoxin units (EU) in one vial) which was appropriately diluted with water for injection (manufactured by Otsuka Pharmaceutical Co., Ltd.) was used.

AL solution

A solution of a freeze-dried product of an AL solution derived from horseshoe crabs of the Limulus genus (the freeze-dried product is referred to hereinafter as LAL, available from Wako Pure Chemical Industries, Ltd., gelation sensitivity: 0.06 EU/ml, for 5 ml) dissolved in 2.5 ml of an LAL-dissolving buffer solution (manufactured by Wako Pure Chemical Industries, Ltd.) was used.

Polyethylene glycol solutions

Prepared by dissolving a polyethylene glycol manufactured by Wako Pure Chemical Industries, Ltd. in water for injection (Otsuka Pharmaceutical Co., Ltd.) so that the concentration became a predetermined value and then subjecting the solution to autoclave treatment (121° C., 15 minutes). It was confirmed that the polyethylene glycol solution was free from endotoxin.

Incidentally, various polyethylene glycols used had the following average molecular weights:

Polyethylene glycol 4,000: weight-average molecular weight of 3,000

Polyethylene glycol 6,000: weight-average molecular weight of 7,500

Polyethylene glycol 20,000: weight-average molecular weight of 20,000

Polyethylene glycol 50,000: weight-average molecular weight of 50,000

Polyethylene glycol 70,000: weight-average molecular weight of 70,000

Polyethylene glycol 500,000: weight-average molecular weight of 500,000

Polyethylene glycol 2,000,000: weight-average molecular weight of 2,000,000

Polyethylene glycol 4,000,000: weight-average molecular weight of 4,000,000.

(Procedure)

In a measuring test tube were placed 0.05 ml of the AL solution, 0.1 ml of the desired polyethylene glycol solution and 0.05 ml of the endotoxin solution (0.2 EU/ml) and the resulting mixture was stirred, after which Toxinometer ET-201 was used to measure the time required until the transmitted light amount ratio ($R_t$) of the liquid mixture (reaction mixture) was reduced by 5% while keeping the temperature at 37° C. (said time is hereinafter referred to as Tg). As a negative control, the same procedure as above was repeated, except that 0.05 ml of water for injection (manufactured by Otsuka Pharmaceutical Co., Ltd.) was substituted for the endotoxin solution, to confirm that the Tg value was more than the measuring time (90 minutes) (gelation was not judged).

Also, previously, a calibration curve showing the relationship between the Tg value and the endotoxin concentration was prepared by placing in a measuring test tube 0.05 ml of the AL solution, 0.1 ml of water for injection (manufactured by Otsuka Pharmaceutical Co., Ltd.) and 0.05 ml of the endotoxin solution having the predetermined concentration, stirring the resulting mixture, and thereafter conducting the measurement in the same manner as above. The Tg values obtained by using the various polyethylene glycol solutions obtained above were applied to the calibration curve to determine the apparent endotoxin concentrations. The apparent endotoxin concentrations thus obtained were applied to the following equation to determine relative activities (%):

Relative activity (%)=(apparent endotoxin conc.)/0.2×100

(Results)

The relative activities (%) obtained when polyethylene glycols having various molecular weights were allowed to be present at various concentrations are shown in Tables 1 to 3. Incidentally, in the Tables, the polyethylene glycol (PEG) concentrations refer to concentrations in the solution during the reaction (during measuring Tg values).

TABLE 1

| PEG conc. | Relative activity (%) | | |
|---|---|---|---|
| (w/w %) | PEG 4,000 | PEG 6,000 | PEG 20,000 |
| 0.156 | 116 | 117 | 120 |
| 0.313 | 124 | 126 | 136 |
| 0.625 | 134 | 160 | 180 |
| 1.25 | 154 | 229 | 308 |
| 2.5 | 222 | 430 | — |
| 5 | — | — | — |

Note: PEG: Polyethylene glycol
—: Since a non-specific turbidity not due to endotoxin was caused, no relative activity was determined.

TABLE 2

| PEG conc. | Relative activity (%) | |
|---|---|---|
| (w/w %) | PEG 50,000 | PEG 70,000 |
| 0.078 | 109 | 105 |
| 0.156 | 119 | 114 |
| 0.313 | 143 | 135 |
| 0.625 | 196 | 204 |
| 1.25 | 322 | 315 |
| 2.5 | — | — |

Note: PEG: polyethylene glycol
—: Since a non-specific turbidity not due to endotoxin was caused, no relative activity was determined.

TABLE 3

| PEG conc. | Relative activity (%) | | |
|---|---|---|---|
| (w/w %) | PEG 500,000 | PEG 2,000,000 | PEG 4,000,000 |
| 0.063 | 97.8 | 98.0 | 96.5 |
| 0.125 | 110 | 113 | 115 |
| 0.25 | 129 | 123 | 121 |
| 0.5 | 203 | 214 | 171 |

Note: PEG: polyethylene glycol

From the results in Tables 1 to 3, it can be seen that the apparent endotoxin concentration is increased, that is, the measurement sensitivity of the endotoxin is increased, by allowing a suitable amount of a polyethylene glycol having a weight-average molecular weight of 3,000 to 4,000,000 to be present when the AL solution is reacted with the endotoxin.

Incidentally, though not shown in the Tables, when the concentration of a high molecular weight polyethylene glycol having a weight-average molecular weight of 500,000 to 4,000,000 exceeds 1.0%, the viscosity of the polyethylene glycol solution becomes high, the handling thereof is difficult, and hence, said polyethylene glycol solution is not practical.

Moreover, though not shown in the Tables, it was found that when a polyethylene glycol having a weight-average molecular weight of 2,000 was used, no effect of accelerating the reaction of the AL solution with the endotoxin was found, and in some cases, said reaction was inhibited. Moreover, such problems appeared that when a polyethylene glycol having a large weight-average molecular weight was used, the viscosity of the reaction mixture became too high, that bubbles were contained in the reaction mixture when the AL solution was poured whereby errors were caused and that the AL solution was attached to the reaction test tube walls to hinder the reaction. Therefore, it has been found that the polyethylene glycol to be used for the purpose of this invention has desirably a weight-average molecular weight of 3,000 to 4,000,000.

EXAMPLE 2

(Reagents)

β-Glucan solution

Carboxymethylated curdlan (manufactured by Wako Pure Chemical Industries, Ltd.) which is a carboxymethylated derivative of (1→3) β-D-glucan was dissolved in water for injection (manufactured by Otsuka Pharmaceutical Co., Ltd.) to prepare a 1 mg/ml solution, and this was appropriately diluted and then used.

AL solution

The freeze-dried product of an LAL solution (available from Wako Pure Chemical Industries, Ltd., gelation sensitivity: 0.06 EU/ml, for 5 ml) was dissolved in 5 ml of an LAL-dissolving buffer solution (manufactured by Wako Pure Chemical Industries, Ltd.), and the resulting solution was used.

Polyethylene glycol solutions

The polyethylene glycol solutions having various concentrations prepared using polyethylene glycol 6,000 in Example 1 were used.

Samples for measurement

An equimolar mixture of β-glucan solution (40 ng/ml) and a polyethylene glycol solution having a predetermined concentration was used as a sample for measurement.

(Procedure)

In a test tube for measurement were placed 0.1 ml of the AL solution and 0.1 ml of the sample for measurement, and the resulting mixture was stirred, after which the Tg of the liquid mixture (reaction mixture) was measured using a Toxinometer ET-201 while the temperature was kept at 37° C. As a negative control, the same procedure as above was repeated, except that the sample for measurement was replaced by 0.1 ml of water for injection (manufactured by Otsuka Pharmaceutical Co., Ltd.) to confirm that the Tg was more than the measurement time (60 minutes) (gelation was not judged).

(Results)

The measurement results are shown in Table 4.

TABLE 4

| Polyethylene glycol concentration (%)* | Tg value (min) |
|---|---|
| 0 | 22.9 |
| 0.5 | 20.2 |
| 1.0 | 18.3 |
| 1.5 | 17.1 |
| 1.8 | 16.4 |
| 2.0 | 16.0 |

Note: *: shows the concentration of the sample for measurement.

From the results in Table 4, it can be seen that the gelation time was shortened, that is, the measurement sensitivity of the β-glucan was increased, by allowing a polyethylene glycol to be present during the reaction.

EXAMPLE 3

(Reagents)

Endotoxin solution

The same as in Example 1.

AL solution

The same as in Example 1.

Polyvinyl alcohol solution

A polyvinyl alcohol having a degree of polymerization of 500 or a polyvinyl alcohol having a degree of polymerization of 2,000 (both manufactured by Wako Pure Chemical Industries, Ltd.) was dissolved in water for injection (manufactured by Otsuka Pharmaceutical Co., Ltd.) to prepare a 2% solution, and this solution was subjected to autoclave treatment at 121° C. for 15 minutes. The polyvinyl alcohol solution thus obtained was used.

Methyl cellulose solution

A methyl cellulose having a viscosity of 15 cps or a methyl cellulose having a viscosity of 100 cps (both manufactured by Wako Pure Chemical Industries, Ltd.) was dissolved in water for injection (manufactured by Otsuka Pharmaceutical Co., Ltd.) to prepare a 2% solution, and this solution was subjected to autoclave treatment at 121° C. for 15 minutes. This solution was thereafter cooled and stirred again to confirm that the methyl cellulose was completely dissolved. The methyl cellulose solution thus obtained was used.

Hydroxypropyl cellulose solution

A hydroxypropyl cellulose having a viscosity of 150 to 400 cps (manufactured by Wako Pure Chemical Industries, Ltd.) was dissolved in water for injection (manufactured by Otsuka Pharmaceutical Co., Ltd.) to prepare a 1% solution, and this solution was subjected to autoclave treatment at 121° C. for 15 minutes. The thus obtained hydroxypropyl cellulose solution was used.

GANTRETZ (a trade name of GAF company for a methyl vinyl ether/maleic anhydride copolymer) solution GANTRETZ AN-119, AN-139 or AN-169 (all manufactured by GAF company) and sodium hydroxide in an amount three times the weight of the GANTRETZ were dissolved in distilled water for injection (Otsuka Pharmaceutical Co., Ltd.) to prepare a 1% solution and this solution was subjected to autoclave treatment at 121° C. for 15 minutes. The thus obtained GANTRETZ solution was used.

Sodium polyacrylate solution

A sodium polyacrylate having a degree of polymerization of 22,000 to 70,000 (manufactured by Wako Pure Chemical Industries, Ltd.) was dissolved in water for injection (manufactured by Otsuka Pharmaceutical Co., Ltd.) to prepare a 0.5% solution, and this solution was subjected to autoclave treatment at 121° C. for 15 minutes. The thus obtained sodium polyacrylate solution was used.

(Procedure)

In a test tube for measurement were placed 0.05 ml of the AL solution, 0.1 ml of the predetermined water-soluble polymer solution and 0.05 ml of the endotoxin solution (0.2 EU/ml) and the resulting mixture was stirred, after which the Tg of the resulting liquid mixture (reaction mixture) was measured using Toxinometer ET-201 while the temperature was kept at 37° C. As a negative control, the same procedure as above was repeated, except that 0.05 ml of water for injection (manufactured by Otsuka Pharmaceutical Co., Ltd.) was substituted for the endotoxin solution to confirm that the Tg value was more than the measurement time (90 minutes) (gelation was not judged).

Also, previously, a calibration curve showing the relation between the Tg value and the endotoxin concentration was prepared by placing 0.05 ml of the AL solution, 0.1 ml of water for injection and 0.05 ml of the endotoxin solution having the predetermined concentration in a test tube for measurement and effecting the measurement in the same manner as above, applying to this calibration curve the Tg values obtained using the various water-soluble polymer solutions obtained above, to determine the apparent endotoxin concentrations. The apparent endotoxin concentrations thus obtained were applied to the following equation to determine relative activity values (%):

Relative activity (%)=(apparent endotoxin conc.)/0.2×100

(Results)

The relative activities (%) obtained using various water-soluble polymers at various concentrations are shown in Table 5 and Table 6. Incidentally, the water-soluble polymer concentrations in the Tables refer to concentrations in the solution during the reaction (during the measurement of Tg values).

TABLE 5

| Polymer | Concentration (%) | Relative activity (%) |
|---|---|---|
| Polyvinyl alcohol Polymn. degree a.500 | 0.625 | 117 |
| | 1.25 | 159 |
| | 2.5 | 235 |
| | 5.0 | — |
| Polyvinyl alcohol Polymn. degree a.2,000 | 0.025 | 113 |
| | 0.25 | 125 |
| | 0.5 | 157 |
| | 1.0 | 242 |
| Methyl cellulose Viscosity: 15 cps | 1.5 | — |
| | 0.125 | 123 |
| | 0.25 | 145 |
| | 0.5 | 213 |
| Methyl cellulose Viscosity 100 cps | 1.0 | 377 |
| | 0.1 | 96.5 |
| | 0.125 | 141 |
| | 0.25 | 159 |
| | 0.5 | 238 |
| Hydroxypropyl cellulose Viscosity: 150–400 cps | 1.0 | 307 |
| | 0.063 | 121 |
| | 0.125 | 130 |
| | 0.25 | 143 |
| | 0.5 | 187 |

TABLE 6

| Polymer | Concentration (%) | Relative activity (%) |
|---|---|---|
| GANTRETZ AN-119 | 0.0005 | 107 |
| | 0.005 | 99.3 |
| | 0.05 | 82.8 |
| | 0.5 | 60.4 |
| GANTRETZ AN-139 | 0.0005 | 99.3 |
| | 0.005 | 92.7 |
| | 0.05 | 79.3 |
| GANTRETZ AN-169 | 0.5 | 107 |
| | 0.0005 | 109 |
| | 0.005 | 97.0 |
| | 0.05 | 92.7 |
| Sodium polyacrylate | 0.5 | 109 |
| | 0.00025 | 108 |
| | 0.0025 | 105 |
| | 0.025 | 95.5 |
| | 0.25 | — |

Note: —: Since a non-specific turbidity not due to endotoxin was caused, relative activity value could not be determined.

From the results in Table 5, it can be seen that the measurement sensitivity of endotoxin is increased when a polyvinyl alcohol having a degree of polymerization of about 500 is allowed to be present at a concentration of 1.25% or more, a polyvinyl alcohol having a degree of polymerization of about 2,000 is allowed to be present at a concentration of 0.25% or more, a methyl cellulose having a viscosity of 15 cps is allowed to be present at a concentration of 0.25% or more, a methyl cellulose having a viscosity of 100 cps is allowed to be present at a concentration of 0.125% or more, or a hydroxypropyl cellulose is allowed to be present at a concentration of 0.125% or more.

On the other hand, from the results in Table 6, it can be seen that such a water-soluble polymer as GANTRETZ which is a methyl vinyl ether/maleic anhydride copolymer, sodium polyacrylate or the like has no such action as to increase the measurement sensitivity of endotoxin.

As is clear from the above description, this invention provides a highly sensitive process for measuring the amount of endotoxin (or β-glucan) using a kinetic turbidimetric method, and when the process of this invention is utilized, endotoxin or β-glucan present in a much smaller amount than in a conventional case can be detected at a high sensitivity. Therefore, this invention contributes greatly to industries.

What is claimed is:

1. A process for determining an amount of endotoxin or of (1→3)-β-D-glucan contained in a sample, which comprises the steps of:

mixing the sample with horseshoe crab amebocyte lysate, in the absence of an ionic surfactant, with at least one water-soluble polymer selected from the group consisting of polyethylene glycol, polyvinyl alcohol, methyl cellulose and hydroxypropyl cellulose, to form a liquid mixture;

applying a light to the liquid mixture;

measuring a time required until a predetermined degree of change in transmittance, in absorbance, or in $R_t$ or log $R_t$, wherein $R_t = I_t/I_0$, and wherein $I_0$ is the amount of initially transmitted light and $I_t$ is the amount of light transmitted after time t elapsed from the mixing of the sample with the amebocyte lysate, or from a predetermined time from the mixing of the sample with the amebocyte lysate; and determining the amount of the endotoxin or of the (1→3)-β-D-glucan contained in the sample by correlating the time measured in the preceding step with a previously prepared calibration curve using the time required for the liquid mixture to reach the aforesaid predetermined degree of change after the mixing of the sample with the amebocyte lysate, or after a predetermined time from the mixing of the sample with the amebocyte lysate.

2. A process according to claim 1, wherein the water-soluble polymer is a polyethylene glycol.

3. A process according to claim 2, wherein the polyethylene glycol has a weight-average molecular weight of 3,000 to 4,000,000.

4. A reagent for measuring an amount of endotoxin or of (1→3)-β-D-glucan contained in a sample, said reagent consisting essentially of horseshoe crab amebocyte lysate and at least one water-soluble polymer selected from the group consisting of polyethylene glycol, polyvinyl alcohol, methyl cellulose and hydroxypropyl cellulose.

* * * * *